(12) United States Patent
Kataoka et al.

(10) Patent No.: US 9,801,958 B2
(45) Date of Patent: Oct. 31, 2017

(54) POLYMER NANOPARTICLE COMPOSITE AND COMPOSITION FOR MRI IMAGING INCLUDING SAME

(71) Applicant: THE UNIVERSITY OF TOKYO, Tokyo (JP)

(72) Inventors: Kazunori Kataoka, Tokyo (JP); Nobuhiro Nishiyama, Tokyo (JP); Horacio Cabral, Tokyo (JP); Peng Mi, Tokyo (JP); Akihiro Kishimura, Tokyo (JP); Yutaka Miura, Tokyo (JP); Ichio Aoki, Chiba (JP); Daisuke Kokuryo, Chiba (JP); Tsuneo Saga, Chiba (JP)

(73) Assignee: THE UNIVERSITY OF TOKYO, Tokyo (JP)

( * ) Notice: Subject to any disclaimer, the term of this patent is extended or adjusted under 35 U.S.C. 154(b) by 0 days.

(21) Appl. No.: 14/913,903

(22) PCT Filed: Aug. 22, 2014

(86) PCT No.: PCT/JP2014/072664
§ 371 (c)(1),
(2) Date: Feb. 23, 2016

(87) PCT Pub. No.: WO2015/025983
PCT Pub. Date: Feb. 26, 2015

(65) Prior Publication Data
US 2016/0206759 A1 Jul. 21, 2016

(30) Foreign Application Priority Data

Aug. 23, 2013 (JP) .................. 2013-173866

(51) Int. Cl.
*A61B 5/055* (2006.01)
*A61K 49/18* (2006.01)
*A61K 49/12* (2006.01)
*C08K 3/32* (2006.01)
*A61K 9/14* (2006.01)

(52) U.S. Cl.
CPC ........ *A61K 49/1872* (2013.01); *A61K 49/128* (2013.01); *A61K 49/1818* (2013.01); *C08K 3/32* (2013.01); *A61K 9/14* (2013.01); *A61K 9/143* (2013.01); *A61K 49/1824* (2013.01); *A61K 49/1851* (2013.01); *A61K 49/1866* (2013.01)

(58) Field of Classification Search
None
See application file for complete search history.

(56) References Cited

U.S. PATENT DOCUMENTS

| 2009/0324494 A1 | 12/2009 | Ham et al. |
| 2010/0278737 A1 | 11/2010 | Kataoka et al. |
| 2012/0114564 A1 | 5/2012 | Hyeon et al. |

FOREIGN PATENT DOCUMENTS

| JP | 2008-143805 A | 6/2008 |
| JP | 2009-531296 A | 9/2009 |
| JP | 2010-516760 A | 5/2010 |

OTHER PUBLICATIONS http://www.merriamwebster.com /dictionary/derivative retrieved on Jan. 25, 2011.*
International Search Report, issued in PCT/JP2014/072664, dated Nov. 11, 2014.
Urano et al., "Selective molecular imaging of viable cancer cells with pH-activatable fluorescence probes", Nature Medicine, Jan. 2009, vol. 15, No. 1, pp. 104-109.
Wesbey et al., "Paramagnetic Pharmaceuticals for Magnetic Resonance Imaging", Physiological Chemistry and Physics and Medical NMR, 1984, vol. 16, No. 2, pp. 145-155.
Written Opinion of the International Searching Authority, issued in PCT/JP2014/072664(PCT/ISA/237), dated Nov. 11, 2014.
Japanese Notice of Reasons for Rejection for Japanese Application No. 2015-532935, dated Jan. 10, 2017, with an English translation thereof.
Extended European Search Report for European Application No. 14837292.3, dated Mar. 29, 2017.
Mi et al., "A pH-Activatable Nanoparticle with Signal-Amplification Capabilities for Non-Invasive Imaging of Tumour Malignancy," Nature Nanotechnology, vol. 11, No. 8, May 2016 (published online May 16, 2016), pp. 1-7 (10 pages total).
Mi et al., "Hydrothermally Synthesized PEGylated Calcium Phosphate Nanoparticles Incorporating Gd-DTPA for Contrast Enhanced MRI Diagnosis of Solid Tumors," Journal of Controlled Release, vol. 174, 2014 (published online Nov. 6, 2013), pp. 63-71.

* cited by examiner

Primary Examiner — James Rogers
(74) Attorney, Agent, or Firm — Birch, Stewart, Kolasch & Birch, LLP

(57) ABSTRACT

The present invention provides a safe polymer nanoparticle composite with few side effects, and an MRI contrast agent incorporating said polymer nanoparticle composite. The polymer nanoparticle composite is capable of specifically accumulating on a tumor tissue to selectively extract the tissue, exhibiting high contrast even when used in small amounts, and enabling imaging over prolonged periods of time. This polymer nanoparticle composite is characterized by containing a block copolymer that includes a non-charged hydrophilic polymer chain segment and an anionic polymer chain segment, and MnCaP.

18 Claims, 9 Drawing Sheets
(4 of 9 Drawing Sheet(s) Filed in Color)

MR image     Image of tissue stained with low-oxygen marker

Before administration   1 hour after administration   2 hours after administration   Excised liver T$_1$-weighted images with lymph node metastasis (1T)

POLYMER NANOPARTICLE COMPOSITE AND COMPOSITION FOR MRI IMAGING INCLUDING SAME

TECHNICAL FIELD

The present invention relates to a polymeric nanoparticle composite incorporating a substance that has MRI contrast ability (MRI imaging ability), as well as an MRI contrast composition (MRI imaging composition), an MRI contrast method (MRI imaging method), and an MRI contrast kit (MRI imaging kit) and the like using the same.

BACKGROUND ART

While cumulative morbidity and mortality of cancers keep rising, early discovery of cancers at any parts is a problem that needs to be solved. Early discovery not only can reduce invasion upon a treatment but also a complete cure can be expected. For patients who have already been diagnosed with progressive cancer, accurate diagnosis of the presence of a distant metastasis is very important for determining the disease stage and for determining the subsequent therapeutic strategy. Examples of a treatment of a cancer include surgical treatment, radiation therapy and chemotherapy, where the surgical treatment can be expected to radically cure the cancer by accurately resecting or ablating the metastatic focus upon the treatment. Also in the case of the radiation therapy, side effects can be alleviated by precisely determining the site of tumor to focus the irradiation and prevent irradiation of a healthy site. In this regard, for any patient at any stage, it is a great advantage to perform correct diagnosis of the cancer site, especially correct diagnosis of the highly malignant cancer.

Typical examples of diagnostic imaging methods for malignant tumors include X-ray computed tomography (CT), ultrasound and magnetic resonance imaging (MRI). These examinations are highly popularized and each has both advantages and disadvantages. Among them, MRI is the most rapidly prevailing diagnostic imaging technology, which importance is particularly increasing recently because it has no problem of radiation exposure or the like, it is capable of visualizing qualitative changes of a soft tissue and it has high objectivity and reproducibility. MRI, however, has difficulty in identifying small tumors because signals of the small tumors are buried in complicated signals of normal tissues only with its hardware. Therefore, in order to enhance the diagnostic accuracy, development of an MRI contrast agent that is capable of selectively extracting a tumor tissue has been a great issue.

Until now, various imaging agents have been developed and put into practical use for increasing the contrast between a tumor tissue and its surrounding tissue. Typical examples of such contrast agents include metal complexes such as Gd-DTPA (gadolinium-diethylenetriamine-pentaacetic acid) (for example, Non-patent Document 1: Wesbey G E, et al. Physiol Chem Phys Med NMR. 1984; 16(2):145-155). Gd-DTPA, however, lacks site specificity, and thus has no targeting property to a specific tissue such as a cancer and rapidly diffuses to respective organs and muscles upon transveous administration. Therefore, it has difficulty in making a definitive diagnosis of a tumor. Gd-DTPA has less side effects through chelation compared to free Gd ion but the dosage and the concentration (500 mM as an undiluted solution) are great. For example, if blood retention in a patient with renal damage or the like is prolonged, Gd is ionized and may pose a risk for causing a serious symptom called nephrogenic systemic fibrosis. Meanwhile, an Mn ion is a contrast agent that enhances contrast for MRI, like Gd-DTPA and else, but if it is transvenously administered alone at the same concentration of Gd-DTPA, serious side effects such as cardiac toxicity are caused. On the other hand, Mn is one of living body essential elements, which does not cause toxicity even when retained in the body in a very small amount and is clinically approved as an oral contrast agent.

Recently, in the field of diagnostic imaging, development of smart function-type probes that are not only capable of simply visualizing a cancer tissue but also capable of depicting the property and the state of the cancer such as the grade of malignancy and cell death has been increasing (for example, Non-patent Document 2: Urano et al., Nat Med. 2009 January; 15(1):104-109). Most of them, however, are fluorescent probes, and there is almost no practical studies regarding MRI contrast agents.

SUMMARY OF THE INVENTION

Under such circumstances, development of an MRI contrast agent that is capable of accumulating specifically at a tumor tissue to selectively depict said tissue, that has high contrast with a use in a small amount, that is capable of imaging for a long period of time, and moreover that has fewer side effects and thus is safe even when circulating in blood for a long period of time has been expected.

The present invention was made giving consideration to the above-described circumstances, and provides a polymer nanoparticle composite, an MRI contrast composition, an MRI contrast method, an MRI contrast kit and the like that are described below.

(1) A polymer nanoparticle composite comprising: a block copolymer comprising a non-charged hydrophilic polymer chain segment and an anionic polymer chain segment; and MnCaP.

In the composite according to (1) above, the anionic polymer chain segment is, for example, a polypeptide having an anionic group on the side chain, whose specific examples being those derived from an anionic polymer selected from the group consisting of poly(glutamic acid), poly(aspartic acid), poly(acrylic acid), poly(methacrylic acid) and poly(malic acid).

In the composite according to (1) above, the non-charged hydrophilic polymer chain segment is, for example, one derived from a hydrophilic polymer selected from the group consisting of polyethylene glycol, poly(2-methyl-2-oxazoline), poly(2-ethyl-2-oxazoline), poly(2-isopropyl-2-oxazoline), polyacrylamide, polymethacrylamide, polyvinyl alcohol, poly(hydroxyethyl acrylate) and poly(hydroxyethyl methacrylate).

The composite according to (1) above may, for example, have a configuration in which MnCaP is incorporated into a nanoparticulate particle that is formed with the above-described block copolymer having the non-charged hydrophilic polymer chain segment as a shell part and the anionic polymer chain segment as a core part.

In the composite according to (1) above, examples of the block copolymer include those represented by General Formula (1-a) or (2-a) below.

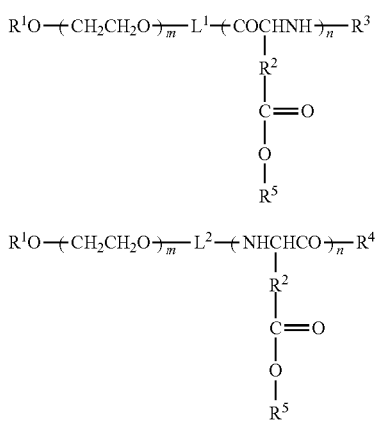

[In Formulae (1-a) and (2-a), $R^1$ represents a hydrogen atom or an unsubstituted or substituted, linear or branched $C_{1-12}$ alkyl group, $L^1$ and $L^2$ represent a linking group, $R^2$ each independently represents a methylene group or an ethylene group, $R^3$ each independently represents a hydrogen atom, a protective group of an amino group, a hydrophobic group or a polymerizable group, $R^4$ represents a hydroxyl group or an initiator residue, $R^5$ each independently represents a hydrogen atom or an alkali metal ion, m represents an integer of 5-20,000, and n represents an integer of 2-5,000].

Examples of the composite according to (1) above include those having an average dispersed particle diameter in an aqueous medium of 30 nm-150 nm as measured by a dynamic light scattering method.

Examples of the composite according to (1) above include polymer nanoparticle composites that release an $Mn^{2+}$ ion under a low pH condition.

(2) An MRI contrast composition comprising the composite according to (1) above.

An example of the composition according to (2) above includes a composition used for detecting a tumor, wherein the tumor is, for example, a primary tumor or a metastatic tumor.

An example of the composition according to (2) above includes a composition used for assessing grade of malignancy of a tumor.

(3) An MRI contrast method comprising a step of administering the composite according to (1) above to a body of a test animal.

An example of the method according to (3) above includes a method used for detecting a tumor, wherein the tumor is, for example, a primary tumor or a metastatic tumor.

An example of the method according to (3) above includes a method used for assessing grade of malignancy of a tumor.

(4) A MRI contrast kit comprising the composite according to (1) above.

An example of the kit according to (4) above includes a kit for detecting a tumor, wherein the tumor is, for example, a primary tumor or a metastatic tumor.

An example of the kit according to (4) above includes a kit for assessing grade of malignancy of a tumor.

BRIEF DESCRIPTION OF DRAWINGS

The patent or application file contains at least one color drawing. Copies of this patent or patent application publication with color drawing will be provided by the USPTO upon request and payment of the necessary fee.

MODES FOR CARRYING OUT THE INVENTION

Figure 1:
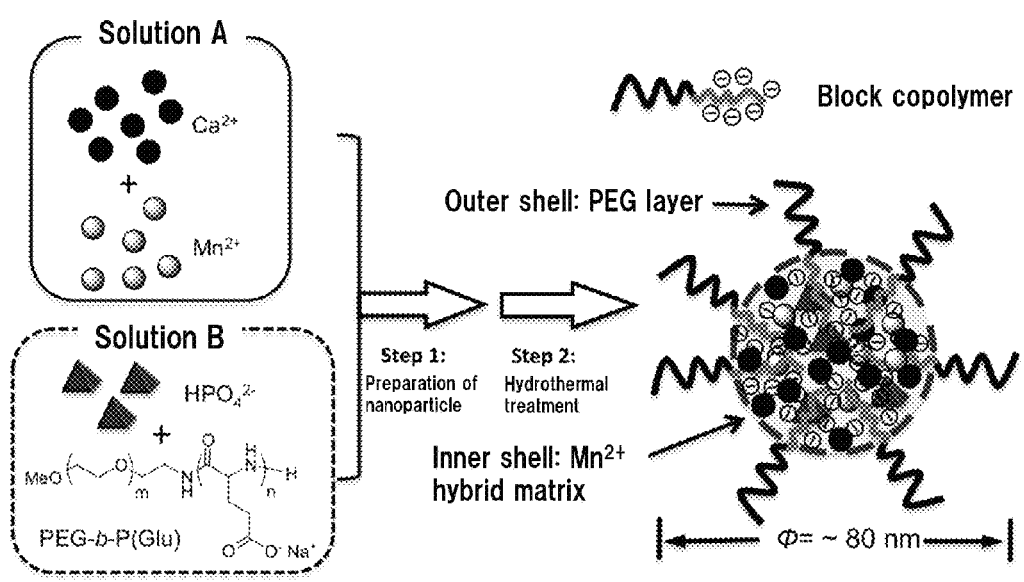
FIG. 1 is a diagram showing an overview of a process of producing a polymer nanoparticle composite according to the present invention.

Hereinafter, the present invention will be described in detail. The scope of the present invention is not limited to these descriptions, and can appropriately be altered and carried out by ways other than the following examples without departing from the spirit of the present invention.

The specification of Japanese Patent Application No. 2013-173866 (filed on Aug. 23, 2013), based on which the present application claims priority, is entirely incorporated herein. In addition, all of the publications, for example, prior art documents, published patent applications, patent publications and other patent documents are incorporated herein by reference.

1. Polymer Nanoparticle Composite

A polymer nanoparticle composite of the present invention was found by focusing on a drug delivery system that utilizes a polymer nanoparticle that has high blood retention property and tumor tissue selectivity (owing to EPR effect). The present invention provides a polymer nanoparticle composite that is obtained by incorporating a specific compound (MnCaP) that is capable of exerting an MRI contrast ability into this polymer nanoparticle.

The polymer nanoparticle composite of the present invention comprises: (1) a block copolymer comprising a non-charged hydrophilic polymer chain segment and an anionic polymer chain segment; and (2) MnCaP as a specific compound capable of exerting an MRI contrast ability. Preferably, a specific configuration of this composite has a configuration in which the above-described MnCaP is incorporated into a nanoparticulate particle that is formed with the above-described block copolymer having the non-charged hydrophilic polymer chain segment of the block copolymer as a shell part and the anionic polymer chain segment as a core part.

According to the present invention, for the sake of convenience, each of the above-described polymer chain segments also comprises a segment that falls into the category of a so-called oligomer chain.

(1) Block Copolymer

In the above-described block copolymer, examples of the non-charged hydrophilic polymer chain segment preferably include, but not limited to, those that are derived from an aqueous polymer selected from the group consisting of polyethylene glycol (PEG), poly(2-methyl-2-oxazoline), poly(2-ethyl-2-oxazoline), poly(2-isopropyl-2-oxazoline), polyacrylamide, polymethacrylamide, polyvinyl alcohol, poly(hydroxyethyl acrylate) and poly(hydroxyethyl methacrylate). Among them, those derived from PEG are more preferable. Since the non-charged hydrophilic polymer chain segment is hydrophilic, it can impart excellent biological compatibility to the polymer nanoparticle composite.

An example of the anionic polymer chain segment in the above-described block copolymer preferably includes, but not limited to, a polypeptide having an anionic group on the side chain. Specifically, preferable examples include those derived from an anionic polymer selected from the group consisting of poly(glutamic acid), poly(aspartic acid), poly(acrylic acid), poly(methacrylic acid) and poly(malic acid), among which those derived from poly(glutamic acid) are more preferable.

Examples of the block copolymer used with the present invention specifically include those represented by General Formula (1) or (2) below.

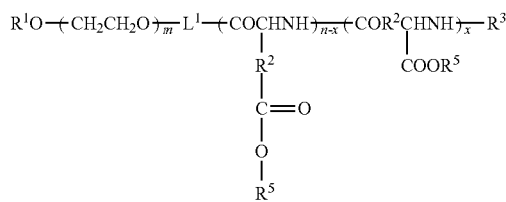

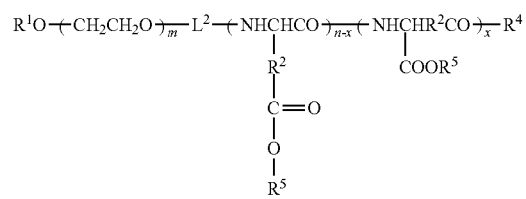

Furthermore, other preferable examples of the block copolymer used with the present invention specifically include those represented by General Formula (1-a) or (2-a) below.

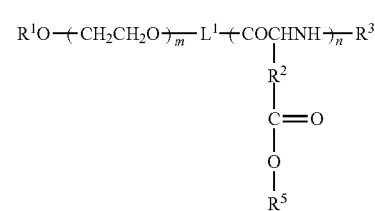

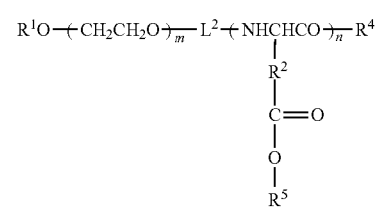

In Formulae (1), (2), (1-a) and (2-a) above, $R^1$ represents a hydrogen atom or an unsubstituted or substituted, linear or branched $C_{1-12}$ alkyl group, $L^1$ and $L^2$ represent a linking group, $R^2$ each independently represents a methylene group or an ethylene group, $R^3$ each independently represents a hydrogen atom, a protective group of an amino group, a hydrophobic group or a polymerizable group, $R^4$ represents a hydroxyl group or an initiator residue and $R^5$ each independently represents a hydrogen atom or an alkali metal ion. Moreover, m represents an integer of 5-20,000 (preferably 10-5,000, more preferably 40-500), and n represents an integer of 2-5,000 (preferably 5-1,000, more preferably 10-200).

The m number of repeat units in Formulae (1), (2), (1-a) and (2-a) above correspond to the non-charged hydrophilic polymer chain segment. The (n-x) and x numbers of repeat units in Formulae (1) and (2) above, and the n number of repeat units in Formulae (1-a) and (2-a) above correspond to the anionic polymer chain segment.

Examples of the above-mentioned unsubstituted or substituted, linear or branched $C_{1-12}$ alkyl group as $R^1$ include, but not limited to, methyl, ethyl, n-propyl, iso-propyl, n-butyl, sec-butyl, tert-butyl, n-pentyl, n-hexyl, decyl and undecyl. Examples of a substituent in a substituted case include an acetalized formyl group, a cyano group, a formyl group, a carboxyl group, an amino group, a $C_{1-6}$ alkoxycarbonyl group, a $C_{2-7}$ acylamide group, and an identical or different tri-$C_{1-6}$ alkylsiloxy group, a siloxy group and a silylamino group. When the substituent is an acetalized formyl group, it can undergo hydrolysis under a mild acid condition to convert into other substituent, i.e., a formyl group (—CHO: or an aldehyde group). Such formyl group or the above-described carboxyl group or amino group can be generated by deprotecting or converting from a corresponding group or moiety in a protected form after preparing the above-described block copolymer. Subsequently, if necessary, it can be covalently linked to a suitable antibody or a fragment (F(ab')$_2$, F(ab), folic acid, etc.) having the specific binding property thereof so as to impart a target-directing property to the block copolymer (and therefore, the polymer nanoparticle composite of the present invention). A non-charged hydrophilic polymer chain segment having such a functional group at one terminal end can be formed, for example, by a method for producing a PEG segment part of a block copolymer described in WO 96/32434, WO 96/33233 or WO 97/06202. The non-charged hydrophilic polymer chain segment formed as such and the anionic polymer chain segment may be linked in any mode via any linking group depending on the method for producing each of the above-described block copolymers. This production method is not particularly limited. In one exemplary production method, a non-charged hydrophilic polymer chain segment having an amino group at the end is used for polymerizing with, for example, an N-carboxylic acid anhydride (NCA) of β-benzyl-L-aspartate and/or γ-benzyl-L-glutamate from the amino terminal end to synthesize a block copolymer. Thereafter, the benzyl side chain group is converted into other ester group or allowed to undergo partial or complete hydrolysis, thereby obtaining a block copolymer of interest. In this case, the structure of the resulting copolymer has a structure of a copolymer that constitutes the block copolymer represented by General Formula (1) or (1-a), where the linking group $L^1$ has a structure derived from the terminal structure of the non-charged hydrophilic polymer chain segment used, which is preferably —(CH$_2$)$_p$—NH— (where, p is preferably an integer of 1-5). Alternatively, an anionic polymer chain segment or a derivative of said polymer chain can be synthesized, which can then be linked to a non-charged hydrophilic polymer chain segment that has been prepared beforehand to produce the copolymer. In this case, it may turn out to have the same structure as one produced by the former method or may have the structure of the block copolymer represented by General Formula (2) or (2-a), wherein a linking group $L_2$ is preferably, but not limited to, —(CH$_2$)$_q$—CO— (where, q is preferably an integer of 1-5).

With respect to $R^3$, examples of the above-described protective group of an amino group include a benzyloxycarbonyl group, a t-butyloxycarbonyl group, an acetyl group and a trifluoroacetyl group. Examples of the hydrophobic group include a benzylcarbonyl group and a benzhydrylcarbonyl group. Furthermore, examples of the polymerizable group include an acryloyl and methacryloyl group.

With respect to $R^4$, an example of the above-described initiator residue includes an aliphatic or aromatic primary amine compound residue (—NH-alkyl) that can serve as an initiator for NCA polymerization.

With respect to $R^5$, examples of the above-described ion of an alkali metal include a sodium (Na) ion, a lithium (Li) ion and a potassium (K) ion.

(2) MnCaP as Specific Compound that can Exert MRI Contrast Ability

MnCaP contained in a polymer nanoparticle composite of the present invention decomposes (dissolves) particularly in a low pH environment and generates a manganese ion (Mn$^{2+}$). Accordingly, an Mn$^{2+}$ ion is released from the polymer nanoparticle composite. As described above, the Mn$^{2+}$ ion has a property such that when it is bound to the surrounding protein, the interaction thereof increases the relaxivity by approximately 10 times or more. Therefore, when the polymer nanoparticle composite of the present invention is used as an MRI contrast agent, it can release an Mn$^{2+}$ ion selectively in the low pH environment of a tumor tissue, it can bind to the protein of the tumor tissue such that the location of the contrast agent is immobilized, and, at the same time, it can bring about an effect of increasing the MRI signal intensity (if not otherwise specified, an MRI signal refers to a signal intensity in T1-weighted imaging). In addition, MnCaP is also capable of accumulating at a normal hepatic tissue in a constant amount without disintegrating, in which case the MRI signal intensity is reduced due to the effect of reduction in the transverse relaxation time. Meanwhile, in a hepatic tumor, it disintegrates in response to the low pH of the hepatic tumor and releases an Mn$^{2+}$ ion, by which the MRI signal intensity is increased and results higher detection ability.

MnCaP can be generated by the reaction (outline) represented by the following formula.

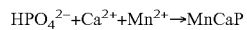

$$HPO_4^{2-} + Ca^{2+} + Mn^{2+} \rightarrow MnCaP$$

Here, the maximum tolerant dose (MTD) of MnCaP for a mouse is about 1.5 mmol/kg. In this regard, the maximum tolerant dose (MTD) of MnCl$_2$ is about 0.22 mmol/kg, which is about ⅐ the maximum tolerant dose (MTD) of MnCaP. Therefore, the polymer nanoparticle composite of the present invention that uses MnCaP is also extremely good for practical use in MRI contrast in terms of maximum tolerant dose (MTD).

(3) Polymer Nanoparticle Composite

Although the method for producing the polymer nanoparticle composite of the present invention is not limited, it is preferably a method in which the above-described block copolymer and raw compounds of MnCaP are mixed to react in an aqueous medium. As the raw compounds of MnCaP, a compound that contains (that generates) HPO$_4^{2-}$, a compound that contains (that generates) Ca$^{2+}$ and a compound that contains (that generates) Mn$^{2+}$ are preferably used.

Any reaction conditions can be employed as long as a polymer nanoparticle composite of interest can be obtained. For example, after the above-described mixing, the resultant is heated (hydrothermally synthesized) preferably at 50-180° C. for 5-120 minutes, more preferably at 80-150° C. for 10-240 minutes and particularly preferably at about 120° C. for about 20 minutes. By this hydrothermal heating, MnCaP is synthesized. An overview of the method for producing this polymer nanoparticle composite is, for example, as shown in FIG. 1.

The aqueous medium as the reaction solvent is preferably water (particularly, deionized water), and it may additionally contain an inorganic or organic buffer, acetonitrile, dimethylformamide, and a water-immiscible organic solvent such as ethanol within a range that does not have adverse influence on the reaction for forming the polymer nanoparticle composite of the present invention.

As to isolation and purification of the produced polymer nanoparticle composite, the composite can be collected from the aqueous medium by a routine method. Typical examples of such method include ultrafiltration, diafiltration and dialysis method.

As described above, the configuration of the polymer nanoparticle composite of the present invention may preferably have a configuration in which MnCaP is incorporated into a nanoparticulate particle that is formed with the above-described block copolymer having the non-charged hydrophilic polymer chain segment as a shell part and the anionic polymer chain segment as a core part. The polymer nanoparticle composite of the present invention usually aggregates in an aqueous medium (aqueous solvent) and takes a form of a solubilized polymeric nanoparticulate. MnCaP, during its production process, can ionically bond with the anionic polymer chain segment of the block copolymer as represented by the following formula (outline).

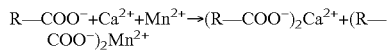
$$R\text{—}COO^-+Ca^{2+}+Mn^{2+}\rightarrow(R\text{—}COO^-)_2Ca^{2+}+(R\text{—}COO^-)_2Mn^{2+}$$

Hence, in the end, MnCaP will be incorporated inside the nanoparticles together with the anionic polymer chain segment composing the core part.

An average dispersed particle diameter of such polymer nanoparticle composite of the present invention in an aqueous medium (as measured by a dynamic light scattering method) is, for example, preferably 30 nm-150 nm, more preferably 30 nm-100 nm and still more preferably 30 nm-80 nm. Such a particle diameter allows exertion of the EPR effect and allows selective accumulation at a tumor tissue.

The content of MnCaP in the polymer nanoparticle composite of the present invention may be, for example, 1-15% by weight, 0.01-5% by weight or 0.3-4.0% by weight in terms of the content of the Mn ion with respect to the composite, and an optimal content can appropriately be provided, without limitation, depending on the magnetic field intensity and contrast conditions of MRI.

2. MRI Contrast Composition and MRI Contrast Method

The present invention provides an MRI contrast composition which comprises the above-described polymer nanoparticle composite of the present invention. The composition of the present invention can be used as a tool for detecting and/or diagnosing a cancer (malignant tumors) by MRI contrast. In some cases, a known compound or composition having an antitumor activity can also be incorporated into the polymer nanoparticle composite so that the resultant can be used as an MRI contrast composition as well as and as an antitumor pharmaceutical composition.

When an MRI contrast composition of the present invention is used, the type of the tumor targeted for detection and the like is not limited, including various known cancer types.

As described above, the MRI contrast composition of the present invention is capable of clearly imaging a low-oxygen area (Hypoxia) at the center of a tumor tissue where a refractory cancer cell is present, and thus can also be used for assessing the grade of malignancy of the tumor.

In addition, since the MRI contrast composition of the present invention is capable of detecting by MRI microcarcinomas (for example, cancers of about 1 mm) that have conventionally been difficult to detect in a tumor-specific manner, it is also capable of detecting and diagnosing primary tumors and metastatic tumors, particularly early primary tumors and metastatic tumors, of various cancers.

In the MRI contrast composition of the present invention, the content of the above-described polymer nanoparticle composite is not limited, and can appropriately be determined in view of the MRI contrast effect.

The MRI contrast composition of the present invention can be applied to various animals such as humans, mice, rats, rabbits, pigs, dogs and cats, and not particularly limited. As a method for administering it to a test animal, parenteral usage such as drip infusion is usually employed, and various conditions including dosage, number of doses and duration of administration can suitably be determined according to the type and the state of the test animal. For example, a small experiment using laboratory animals or volunteers is preferably carried out as necessary so that the dose in a case of intravenous administration to human is determined by a physician considering the results thereof as well as the state of the patient. In general, the dose may be 1.0-10,000 mg/m² once a day.

In view of the application to MRI contrast, the MRI contrast composition of the present invention can be used with appropriately selected excipient, filler, extender, binder, wetting agent, disintegrator, lubricant, surfactant, dispersant, buffer, preservative, dissolution adjuvant, antiseptic, flavoring agent, analgesic, stabilizer, isotonic agent or else that are generally used in pharmaceutical manufacturing.

The present invention can also provide an MRI contrast method (in particular, an MRI contrast method for detecting a tumor and an MRI contrast method for detecting an primary tumor or a metastatic tumor) that comprises a step of administering the polymer nanoparticle composite of the present invention or the MRI contrast composition of the present invention to the body of a test animal, as well as a method for assessing grade of malignancy of a tumor by utilizing said method. These methods may appropriately comprise other steps based on knowledge and technical standard of conventional MRI contrast. Examples of such steps include a step of carrying out MRI examination on a test animal after or simultaneously with the administration and a step of detecting the presence or absence of a tumor based on the results (image) obtained by said examination.

3. MRI Contrast Kit

A MRI contrast kit of the present invention is characterized by comprising the above-described polymer nanoparticle composite of the present invention. This kit can favorably be used in the above-described MRI contrast method and the method for assessing grade of malignancy of a tumor utilizing said method.

In this kit, the storage state of the polymer nanoparticle composite of the present invention is not limited, and a state such as a solution form or a powder form can be selected considering the stability (preserving property) and ease of use.

The MRI contrast kit of the present invention may include components other than the above-described polymer nanoparticle composite. Examples of other component include, but not limited to, various buffers, an antiseptic, a dispersant, a stabilizer and an instruction (user manual).

Hereinafter, the present invention will be described more specifically by way of examples although the present invention is not limited thereto.

EXAMPLE 1

<Production of MnCaP Nanoparticle Composite (Polymer Nanoparticle Composite)>

An MnCaP nanoparticle composite was produced by utilizing the chemical reaction represented by the following formula and further by going through a two-stage procedure, i.e., composite formation and hydrothermal treatment, as shown in FIG. 1 (schematic view).

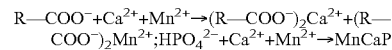
$$R\text{—}COO^-+Ca^{2+}+Mn^{2+}\rightarrow(R\text{—}COO^-)_2Ca^{2+}+(R\text{—}COO^-)_2Mn^{2+};HPO_4^{2-}+Ca^{2+}+Mn^{2+}\rightarrow MnCaP$$

First, solution A was prepared by dissolving 250 mM of $Ca^{2+}$ and 20 mM of $Mn^{2+}$ in a Tris-HCl buffer (pH 7.6). Next, solution B was prepared by dissolving 5 mM of a polyethylene glycol-poly(glutamic acid) block copolymer (PEG-b-P(Glu)) in 50 mM of HEPES buffer saline (pH 7.1) containing 6 mM of $HPO_4^{2+}$. The same volumes of solution A and solution B were agitated to be mixed for 5 seconds using a vortex mixer to prepare the MnCaP nanoparticle composite. The resulting MnCaP nanoparticle composite solution was subjected to a hydrothermal treatment for 20 minutes using an autoclave set to 120° C. The resulting MnCaP nanoparticle composite was dialyzed against 25 mM HEPES buffer Saline (pH7.4) and then purified by ultrafiltration using a HEPES buffer.

The structure of the above-described PEG-b-P(Glu) is as follows.

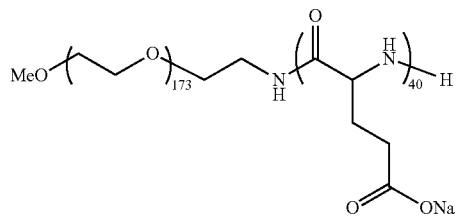

EXAMPLE 2

<Method>
1. Measurement of Relaxivity of MnCaP Nanoparticle Composite and Comparison with Existing $MnCl_2$ in Solution In order to measure the relaxivity of the produced MnCaP nanoparticle composite and compare the contrast effect with existing $MnCl_2$ alone, a preclinical permanent magnet type 1T (Tesla) MR equipment (Icon™, Bruker-Biospin, Germany) was used to measure the relaxivity and acquire $T_1$-weighted images for comparison. For the measurements, the MnCaP nanoparticle composite at a concentration of 0.1-0.5 mM and $MnCl_2$ at the same concentration were used and measured in PCR sample tubes. Distilled water was used for dilution.

The relaxivity was measured using a proton volume coil (inner diameter 35 mm). As the contrast method, a rapid spin-echo technique adopting inversion pulse (Rapid Acquisition with Relaxation Enhancement, RARE) was employed. Parameters used for the imaging were as follows.
Echo Time (TE)=10 ms;
Repetition Time (TR)=16,000 ms;
Inversion Time (TI)=49.59, 75, 100, 150, 200, 300, 400, 600, 800, 1000, 1200, 1600, 2400, 3200, 6400 ms;
RARE Factor=8;
Field of View (FOV)=48.0×48.0 $mm^2$;
Slice thickness=2.0 mm;
Number of pixels=256×256;
Imaging direction=Horizontal;
Summation times=1;
Imaging time per TI=8 minutes and 32 seconds ($T_1$-weighted image was acquired by using a spin-echo technique with the following imaging parameters: TE=10.0 ms; TR=400 ms);
FOV=48.0×48.0 $mm^2$;
Slice thickness=2.0 mm;
Number of pixels=256×256;
Imaging direction=Horizontal;
Summation times=8;
Imaging time=13 minutes and 39 seconds
2. Evaluation of Tumor Accumulating Property Using Subcutaneous Tumor Model Mouse In order to examine the tumor accumulating property of the produced MnCaP nanoparticle composite, the MnCaP nanoparticle composite was administered to model mice that were subcutaneously transplanted with tumor cells to visualize changes in the MRI images of the tumors. The above-described preclinical permanent magnet-type 1T-MR equipment and a proton volume coil were used for MRI. The tumor model mice were produced by subcutaneously transplanting mouse-derived colon cancer cell Colon26 into the buttocks of female BALB/c nude mice (Japan SLC) at $1.0×10^6$ cells/50 μl. For the experiment, a model mouse that had a tumor size of about 5-10 mm on 7th-9th day after the transplantation was used.

MR imaging was carried out by a spin-echo technique, where the parameters used were as follows.
TE=11.5 ms;
TR=400 ms;
FOV=44.0×44.0 $mm^2$;
Slice thickness=1.0 mm;
Number of pixels=256×256;
Imaging direction=Transaxial;
Summation times=4;
Imaging time=6 minutes and 49 seconds
MR imaging was carried out continuously before the administration to 4 hours after the administration of the MnCaP nanoparticle composite. The MnCaP nanoparticle composite was prepared to have an Mn concentration of 0.22 mmol/kg, and administered to the mouse tail vein. An isoflurane inhalation anesthetic (1.0-2.0%) was used during the imaging to keep the mice from moving. Moreover, a thermocouple thermometer was inserted into the mouse rectum to keep the body temperature at 36-37° C. using a self-built warm water circulation system.
3. Comparing Immunostained Tissue Image that Detects Low-Oxygen Area with MR Image In order to assess that the produced MnCaP nanoparticle composite is responsive to pH decrease, an immunostained tissue image that detects a low-oxygen area with low pH within a tumor was compared with MR images acquired upon administration of the MnCaP nanoparticle composite. As a marker for detecting the low-oxygen area, Hypoxyprobe™-1 (HPI) containing 2-nitroimidazole-based compound Pimonidazole was used. Hypoxyprobe™-1 was administered to the tail vein of the tumor model mouse at a concentration of 60 mg/kg before the administration of the MnCaP nanoparticle composite. The MR image upon administering the MnCaP nanoparticle composite was acquired using the same experimental protocol/parameters as those in item 2. above. MR images were continuously acquired until 4 hours after the administration of the MnCaP nanoparticle composite. Thereafter, the tumor subcutaneously transplanted into the model mouse was resected and histologically fixed using a 4% paraformaldehyde/phosphate buffer. Paraffin embedding and immunostaining of the tissue using an anti-Pimonidazole antibody were performed to compare the MR images with the image acquired with an inverted stereomicroscope.
4. Comparing Image of Hyperlactate Metabolism Region Acquired by Chemical Shift Imaging Technique with MR Images In a region within a tumor where low oxygenation had advanced, lactic acid (Lactate) of the tissue increases due to anaerobic metabolism. Since lactic acid has low pH, a tissue that shows a large amount of lactic acid can serve as a marker that suggests low oxygen and low pH associated with low blood circulation. Therefore, MR spectroscopy (MRS) was utilized to examine whether the regions with increasing signal intensities match between a lactate metabolism image acquired by chemical shift imaging (CSI) that illustrates signal intensities in the chemical shift region of the lactic acid and the MR images acquired upon administering the MnCaP nanoparticle composite.

The CSI image was acquired by using a preclinical superconducting magnet-type 7.0T-MR equipment (Biospec, Bruker-Biospin) and a cooling coil (CryoProbe™, Bruker-Biospin). Upon CSI imaging, PRESS (Point-RE-Solved Spectroscopy) technique for MRS was used to suppress a signal from a proton by VAPOR (variable pulse power and optimized relaxation delays) technique. Parameters used for imaging were as follows.

TE=20 ms;
TR=3,000 ms;
FOV=14.1+14.1 mm$^2$;
Slice thickness=1.5 mm;
Number of acquired data: 10×10;
Number of pixels in reconstruction image: 16×16;
Imaging time: 12 minutes 48 seconds (after acquiring the CSI image, the tumor model mouse was transferred into 1T-MR equipment to acquire MR images before and after the administration of the MnCaP nanoparticle composite. The imaging parameters were the same as those in item 2. above).

5. Detection of Microtumor in Liver Metastatic Model Mouse

In order to evaluate the tumor detecting ability of the MnCaP nanoparticle composite with respect to metastatic/microtumors, liver metastatic model mice were used to assess the detection of liver metastatic tumors. The liver metastatic models were generated by transplanting mouse-derived colon cancer cell Colon26 into spleens of female BALB/c nude mice (Japan SLC) for $1.0×10^6$ cells/50 µl. The experiment was carried out on 7th-9th day after the transplantation. The dosage of the MnCaP nanoparticle composite was 0.22 mmol/kg in terms of Mn concentration, which was administered via the mouse tail vein. MR imaging was carried out in the same way as that in item 2. above. Parameters used for imaging were as follows.

TE=11.5 ms;
TR=400 ms;
FOV=85.0×85.0 mm$^2$;
Slice thickness=1.0 mm;
Number of pixels=256×256;
Imaging direction=Horizontal;
Summation times=4;
Imaging time=6 minutes and 49 seconds <Results/Reviews>

Figure 2:
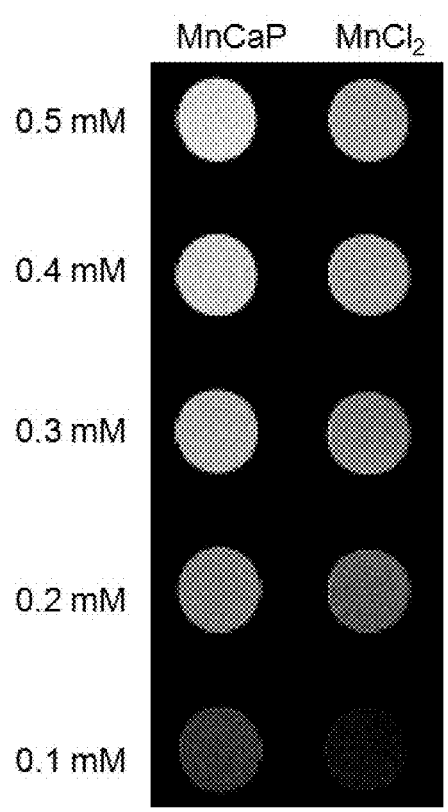
FIG. 2 is an image used for assessing the contrast effects of a prepared MnCaP nanoparticle composite and an $MnCl_2$ solution. The signal intensity of the MnCaP nanoparticle solution was almost equivalent to or slightly higher than that of the $MnCl_2$ solution at the same concentration.

1. Measurement of Relaxivity of MnCaP Nanoparticle Composite and Comparison with Existing MnCl$_2$ in Solution The T$_1$-weighted images of the MnCaP nanoparticle composite and the MnCl$_2$ solution are shown in FIG. 2. The signal intensity of the MnCaP nanoparticle composite was almost equal to or slightly higher (by about 10-27%) than the signal intensity of the MnCl$_2$ solution at the same Mn$^{2+}$ concentration. The measured longitudinal relaxivity $_{r1}$ was 6.5-11.10 mM$^{-1}$ s$^{-1}$ for the MnCaP nanoparticle composite and 7.30-7.58 mM$^{-1}$ s$^{-1}$ for the MnCl$_2$ solution, confirming that the produced MnCaP nanoparticle composite had equal or slightly higher contrast effect when compared to the MnCl$_2$ solution. Since this result shows that the MnCaP nanoparticle composite had similar level of signal intensity to that of the MnCl$_2$ solution even in a state before being disintegrated, a moderate increase in the MR signal intensity at the accumulated site can be expected according to the dynamic state of the MnCaP nanoparticle composite.

Figure 3:
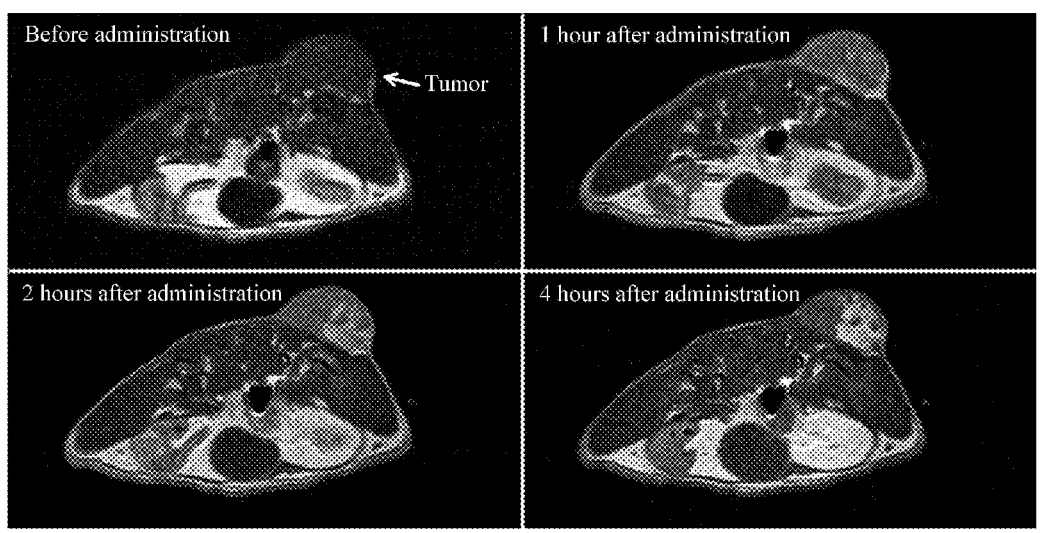
FIG. 3 shows 1T (Tesla)-MR images acquired before and after the administration of the MnCaP nanoparticle composite to a tumor model mouse that was subcutaneously implanted with mouse-derived colon cancer cell Colon26.
Figure 4:
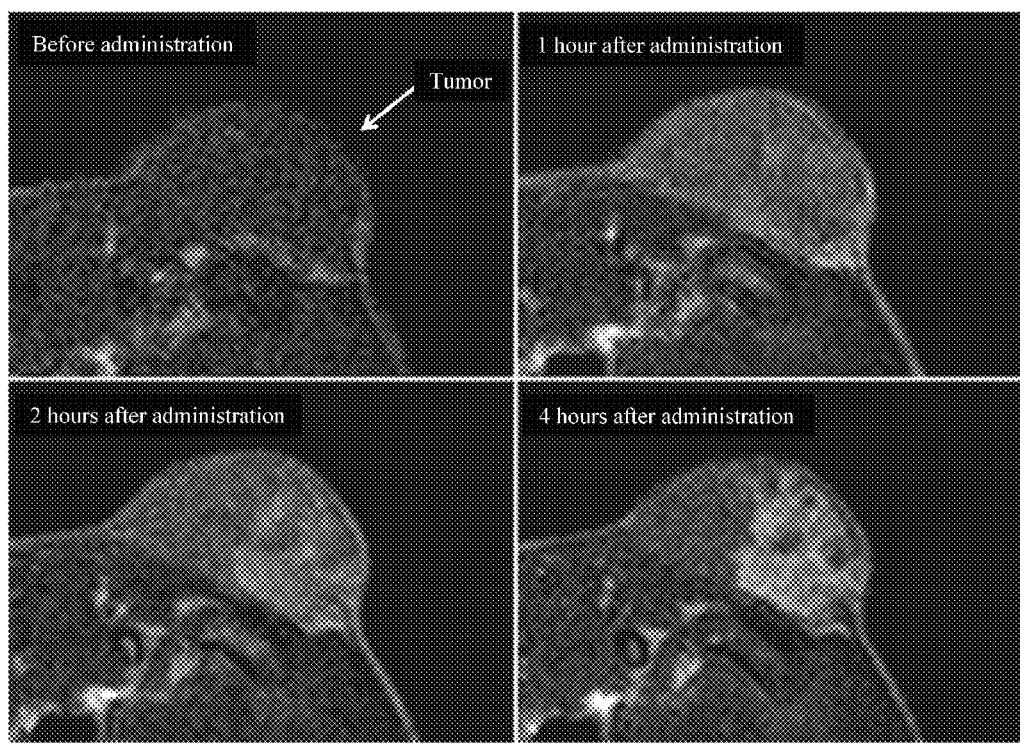
FIG. 4 shows enlarged views of the tumor region in the 1T-MR images acquired before and after the administration of the MnCaP nanoparticle composite to the tumor model mouse that was subcutaneously implanted with mouse-derived colon cancer cell Colon26.

2. Evaluation of Tumor Accumulating Property Using Subcutaneous Tumor Model Mouse The 1T-MR images of the trunk of the mouse including the tumor region and the enlarged 1T-MR images of the tumor region, before the administration to 4 hours after the administration of the MnCaP nanoparticle composite, are shown in FIGS. 3 and 4, respectively. While the signal intensity in the tumor region before the administration was equal to the surrounding muscle region, the MR signal intensity within the tumor moderately increased almost uniformly after the administration (about 45% increase as compared to the signal ratio before the administration). This was considered to have resulted because the administered MnCaP nanoparticle composite accumulated at the tumor while the signal from the MnCaP nanoparticle composite present in the capillary blood vessels also contributed to the signal increase. Two and the following hours after the administration, an extremely great signal increase was observed in a part of the tumor region (about 120% increase as compared to the signal ratio before the administration). This was considered to have resulted because Mn$^{2+}$ was released as the MnCaP nanoparticle composite was dissolved in a region having pH lower than that of the normal tissue, where the contrast effect increased due to interaction with the surrounding protein and the like. Binding between Mn$^{2+}$ and protein has been reported to restrict the molecular motion and greatly enhance the relaxivity (Document: Koylu M Z, Asubay S, Yilmaz A. Determination of Proton Relaxivities of Mn(II), Cu(II) and Cr(III) added to Solutions of Serum Proteins. Molecules, 2009;14(4):1537-1545).

Figure 5:
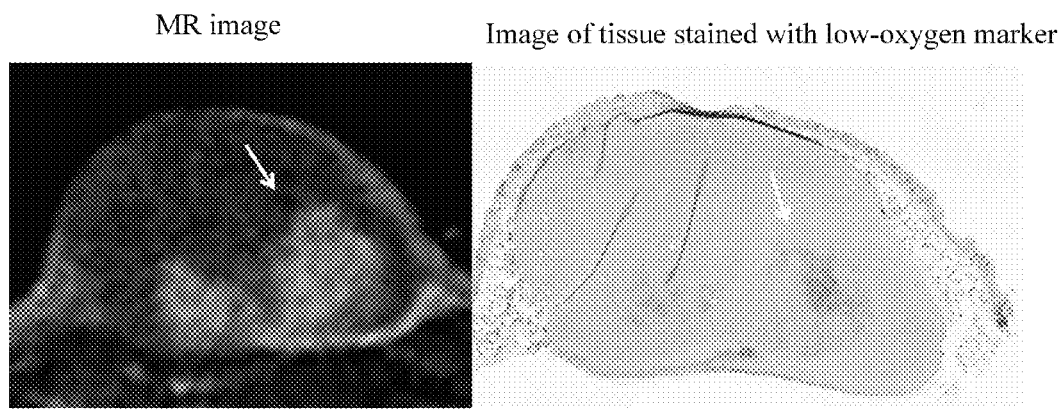
FIG. 5 shows an MR image (left) acquired after the administration of the MnCaP nanoparticle composite to the tumor model mouse that was subcutaneously implanted with mouse-derived colon cancer cell Colon26, and an image of immunostained tissue (right) acquired using Pimonidazole at the same location. The specifically white region in the MR image coincided with the brown region in the stained tissue image (white arrows).

3. Comparing Immunostained Tissue Image that Detects Low-Oxygen Area with MR Image The MR image acquired after the administration of the MnCaP nanoparticle composite and an immunostained tissue image acquired using Pimonidazole to detect a low-oxygen area are shown in FIG. 5. The region with higher signal intensity compared to the surrounding region in the MR image matched well with the positive (brown) low oxygen/low pH region in the Pimonidazole immunostained tissue image. From this, the contrast effect by Mn$^{2+}$ was considered to have increased with the result that the MnCaP nanoparticle composite used was dissolved due to the decreased pH in the low-oxygen area.

Figure 6:
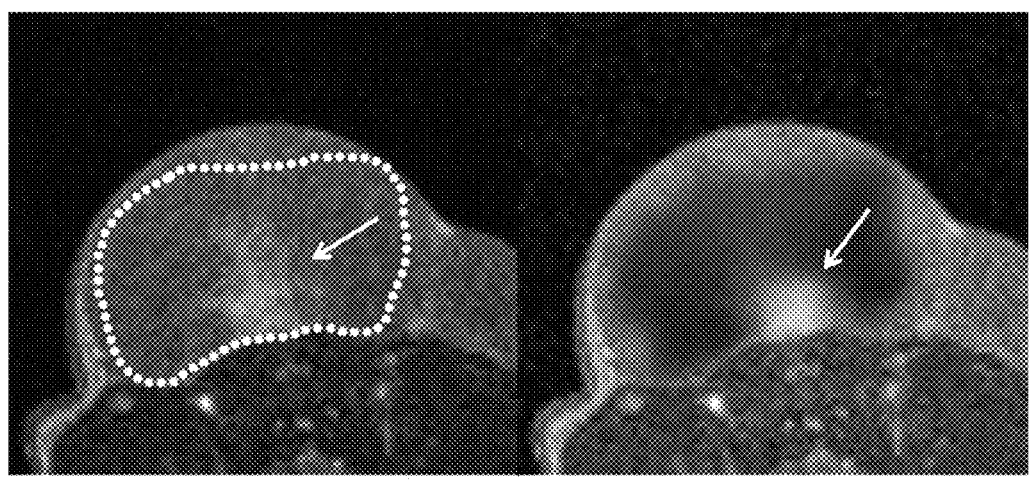
FIG. 6 shows an MR image (left) acquired after the administration of the MnCaP nanoparticle composite to the tumor model mouse that was subcutaneously implanted with mouse-derived colon cancer cell Colon26, and an image (right) acquired by superimposing a chemical shift image that illustrates the signal intensities in the chemical shift region of lactic acid. The region rich in lactic acid (right image, white) coincided with the white region in the MR image (white arrow).

4. Comparing Image of Hyperlactate Metabolism Region Acquired by Chemical Shift as Imaging Technique with MR Images The hyperlactate metabolism region image acquired by the chemical shift imaging technique before the administration of the MnCaP nanoparticle composite and the 1T-MR image acquired after the administration of the MnCaP nanoparticle composite are shown in FIG. 6. The region showing a hyperlactate distribution acquired by the chemical shift imaging technique matched well with the region where the signal intensity specifically increased in the MR image of the tumor acquired after the administration of the MnCaP nanoparticle composite. This suggested that the contrast effect by Mn$^{2+}$ increased because the accumulated MnCaP nanoparticle composite was dissolved in the low-oxygen area where lactic acid was largely generated due to anaerobic metabolism.

5. Detection of Microtumor in Liver Metastatic Model Mouse

Figure 7:
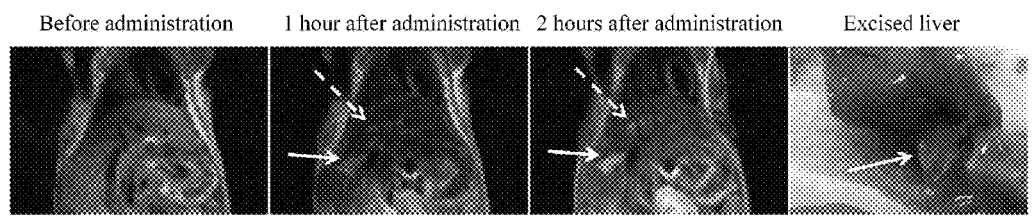
FIG. 7 shows MR images before, and 1 and 2 hours after the administration of the MnCaP nanoparticle composite to a liver metastatic model mouse, and a picture of the excised liver. After the administration of the MnCaP nanoparticle composite, the metastatic tumor was emphasized in white (white arrows). This also coincided with the tumor in the excised liver (white solid arrow). In addition, the small blood vessels in the liver were also depicted after an hour following the administration.

The 1T-MR images acquired before and after the administration of the MnCaP nanoparticle composite to the liver metastatic model mouse and the solid organ of the liver excised after the experiment are shown in FIG. 7. In the 1T-MR images after the administration of the MnCaP nanoparticle composite, the signal in the normal liver region decreased while the signal of the tumor region increased. The region where the signal increased matched with the region in the excised organ where the tumor was present.

The change in the signal of the normal liver region appears to be a decrease of the positive contrast effect of $Mn^{2+}$ due to the effect of shortening of the transverse relaxation time caused by the highly accumulated MnCaP nanoparticle composite. Meanwhile, in the tumor region, the MnCaP nanoparticle composite accumulated and dissolved in response to the pH change, resulting in an increasing effect due to $Mn^{2+}$. Gd-EOB-DTPA that is currently used in clinical practice detects a tumor by utilizing its property of indicating a normal liver region in white with almost no change in the tumor region. On the other hand, the MnCaP nanoparticle composite gave an MR image where the tumor region was indicated in white with greater contrast due to the decreased signal of the surrounding normal tissue. From this, the MnCaP nanoparticle composite was considered to be useful for detecting a microscopic liver metastatic tumor. Furthermore, since the MnCaP nanoparticle composite has a longer half-life in blood, it also has blood vessel contrast effect. This feature appears to be useful not only for imaging a tumor but also the nutrient vessels leading to the tumor so that the property of the tumor and the therapeutic effect can be assessed.

EXAMPLE 3

<Method>

Figure 8:
FIG. 8 shows images of a prepared lymph node metastasis model mouse (tumor model mouse). (a) A picture of luciferase luminescence from a tumor that had metastasized to the lymph node, observed with a photon imager, and (b) a picture of an anatomically observed tumor that had metastasized to the lymph node.
Figure 8:
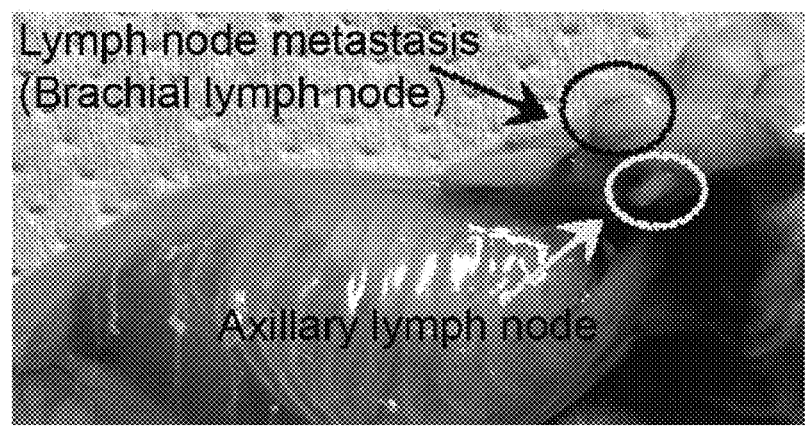

In order to evaluate the lymph node imaging with the produced MnCaP micellar composite, the composite was administered to a prepared node metastasis model mouse (tumor model mice) (see FIG. 8) to compare the signal change thereof. For MRI, a preclinical permanent magnet-type 1T-MR equipment and a proton volume coil were used.

The tumor model mouse was produced by transplanting $2.0 \times 10^6/10$ μl of mouse breast cancer cells that had been introduced with luciferase gene, i.e., 4T1-Luc cells, into the back of the left front limb of a female BALB/c mouse. The experiment was carried out on 16th days after the transplantation.

MR imaging was carried out by a spin-echo technique, where the parameters used were as follows.
TE=10.6 ms;
TR=400 ms;
FOV=40.0×40.0 $mm^2$;
Slice thickness=1.0 mm (with no slice gap)
Number of pixels=256×256;
Imaging direction=Transaxial;
Summation times=4;
Imaging time=6 minutes and 49 seconds The MR imaging was carried out continuously before the administration to 2 hours after the administration of the MnCaP micellar composite. The MnCaP micellar composite was prepared to have an Mn concentration of 0.22 mmol/kg, and administered to the mouse tail vein. An isoflurane inhalation anesthetic (1.0-2.0%) was used during the imaging to keep the mice from moving. Moreover, a thermocouple thermometer was inserted into the mouse rectum to keep the body temperature at 36-37° C. using a self-built warm water circulation system.

<Results>

Figure 9:
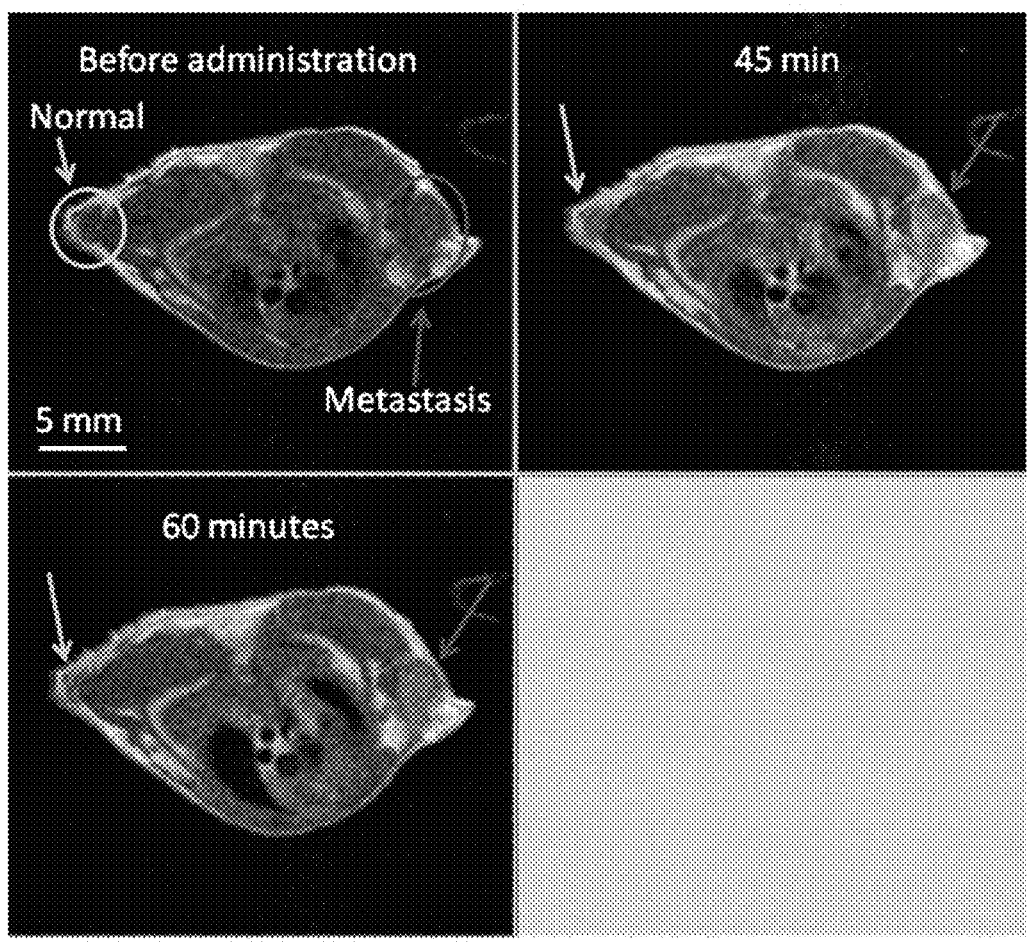
FIG. 9 shows 1T-MR images including a normal lymph node (Normal; yellow arrow) and a lymph node metastasis site (Metastasis; red arrow) before and 45 and 60 minutes after the administration of a MnCaP micellar composite.

1T-MR images including lymph node metastasis sites before, and 45 and 60 minutes after the administration of the MnCaP micellar composite are shown in FIG. 9. While the signal in the tumor region before the administration was equivalent to that in the surrounding muscle tissue, the MR signal intensity in the lymph node metastasis site (Metastasis; red arrow) after the administration was found increased (changed into white). This was considered to be caused because the administered MnCaP micellar composite accumulated at the lymph node metastasis site where the released manganese contrast agent bonded to the cancer tissue, thereby enhancing the signal. On the other hand, in the normal lymph node (Normal; yellow arrow), a localized signal was observed in a minimal part of the lymph node after the administration, but it remained within an extremely localized range (probably marginal sinus and medullary lymphatic sinus) caused by passive inflow.

INDUSTRIAL APPLICABILITY

The present invention can provide a safe MRI contrast composition (MRI contrast agent) with less side effects which is capable of specifically accumulating at a tumor tissue to selectively depict the tissue, capable of exhibiting high contrast even when used in a small amount, and capable of imaging over prolonged periods of time, as well as a polymer nanoparticle composite and the like used for said composition.

The MRI contrast composition (and thus the polymer nanoparticle composite) of the present invention has a property of being dissolved in response to pH, and thus it can release a manganese ion ($Mn^{2+}$) in a low pH environment. Here, the released $Mn^{2+}$ ion has a property of increasing the relaxivity for about 10 times due to interaction with the surrounding protein. Therefore, the MRI contrast composition of the present invention can selectively release $Mn^{2+}$ ion in a low pH environment of a tumor tissue, and exerts an effect of enhancing the MRI signal intensity.

Specifically, for example, the MRI contrast composition of the present invention can increase the contrast of a whole tumor tissue (enhances the MRI signal intensity) in about 2 hours after the administration, and thereafter particularly increases the contrast of the center portion of the tumor tissue to a remarkable extent. This center portion is a low-oxygen area (Hypoxia) where pH is particularly lowered due to acidosis (also confirmed by immunostaining) and the grade of malignancy is known to be high due to the presence of a refractory cancer cell. Therefore, the MRI contrast composition of the present invention could be the world's first probe that can clearly image hypoxia when a refractory cancer cell is present inside with high contrast by administering a small amount of the contrast agent. This also means that it also allows assessment of the grade of malignancy of the tumor.

Furthermore, since the MRI contrast composition of the present invention can detect microcarcinoma (for example, cancer of about 1 mm) that has conventionally been difficult to detect by MRI, it also allows early discovery of an early primary tumor and a metastatic tumor. In particular, in a case of liver cancer, it has a property of being capable of forming a greater contrast, by lowering the signal in the normal hepatic tissue due to shortening of the transverse relaxation time while increasing the signal in the liver cancer region due to Mn release.

Hence, the MRI contrast composition (and thus the polymer nanoparticle composite) according to the present invention is extremely useful in that it can realize an MRI contrast method that can diagnose a cancer with unconventionally high accuracy.

The invention claimed is:

1. A polymer nanoparticle composite comprising: a block copolymer comprising a non-charged hydrophilic polymer chain segment and an anionic polymer chain segment; and MnCaP;

wherein the anionic polymer chain segment is a polypeptide having an anionic group on a side chain of the polypeptide; and wherein the non-charged hydrophilic polymer chain segment is selected from the group consisting of polyethylene glycol, poly(2-methyl-2-oxazolineT poly(2-ethyl-2-oxazolineT poly(2-isoprot>yl-2-oxazoline), polyacrylamide, polymethacrylamide, polyvinyl alcohol, polvthvdroxyethyl acrylate) and polv(hvdroxy ethyl methacrylate).

2. The composite according to claim 1, wherein the anionic polymer chain segment is derived from an anionic polymer selected from the group consisting of poly(glutamic acid) and poly(aspartic acid).

3. The polymer nanoparticle composite according to claim 1, which has a configuration in which MnCaP is incorporated into a nanoparticulate particle that is formed with the block copolymer having the non-charged hydrophilic polymer chain segment as a shell part and the anionic polymer chain segment as a core part.

4. The polymer nanoparticle composite according to claim 1, wherein the block copolymer is represented by General Formula (1-a) or (2-a) below:

(1-a)

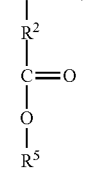

(2-a)

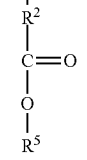

wherein $R^1$ represents a hydrogen atom or an unsubstituted or substituted, linear or branched $C_{1-12}$ alkyl group, $L^1$ and $L^2$ represent a linking group, $R^2$ each independently represents a methylene group or an ethylene group, $R^3$ each independently represents a hydrogen atom, a protective group of an amino group, a hydrophobic group or a polymerizable group, $R^4$ represents a hydroxyl group or an initiator residue, $R^5$ each independently represents a hydrogen atom or an alkali metal ion, m represents an integer of 5-20,000, and n represents an integer of 2-5,000.

5. The polymer nanoparticle composite according to claim 1, whose average dispersed particle diameter in an aqueous medium is 30 nm-150 nm as measured by a dynamic light scattering method.

6. The polymer nanoparticle composite according to claim 1, wherein the polymer nanoparticle composite releases an $Mn^{2+}$ion.

7. An MRI contrast composition comprising the polymer nanoparticle composite according to claim 1.

8. The composition according to claim 7, which is used for detecting a tumor.

9. The composition according to claim 8, wherein the tumor is a primary tumor or a metastatic tumor.

10. The composition according to any one of claims 7-9, which is used for assessing grade of malignancy of a tumor.

11. An MRI contrast method comprising a step of administering the polymer nanoparticle composite according to claim 1 to a body of a test animal.

12. The method according to claim 11, which is used for detecting a tumor.

13. The method according to claim 12, wherein the tumor is a primary tumor or a metastatic tumor.

14. The method according to any one of claims 11-13, which is used for assessing grade of malignancy of a tumor.

15. A MRI contrast kit comprising the polymer nanoparticle composite according to claim 1.

16. The kit according to claim 15, which is useful for detecting a tumor.

17. The kit according to claim 16, wherein the tumor is a primary tumor or a metastatic tumor.

18. The kit according to any one of claims 15-17, which is useful for assessing grade of malignancy of a tumor.

* * * * *